(12) United States Patent
Lu

(10) Patent No.: US 7,105,643 B2
(45) Date of Patent: Sep. 12, 2006

(54) MONOCLONAL ANTIBODIES SPECIFIC FOR CRACK COCAINE METABOLITES, A CELL LINE PRODUCING THE SAME, AND CRACK COCAINE CONJUGATES

(75) Inventor: Natalie T. Lu, Clarksville, MD (US)

(73) Assignee: The United States of America as represented by the Attorney General of the Dept. of Justice, Washington, DC (US)

( * ) Notice: Subject to any disclaimer, the term of this patent is extended or adjusted under 35 U.S.C. 154(b) by 623 days.

(21) Appl. No.: 10/629,749

(22) Filed: Jul. 30, 2003

(65) Prior Publication Data
US 2005/0026303 A1    Feb. 3, 2005

(51) Int. Cl.
C07K 16/44    (2006.01)
C07K 1/13     (2006.01)
C12N 5/18     (2006.01)
C12N 5/20     (2006.01)
G01N 33/531   (2006.01)

(52) U.S. Cl. .................. 530/388.9; 530/403; 530/409; 530/807; 530/809; 435/70.21; 435/345; 435/354; 435/961; 436/548

(58) Field of Classification Search ............ 530/388.9, 530/403, 409, 807, 809; 435/70.21, 345, 435/354, 961; 436/548
See application file for complete search history.

(56) References Cited

U.S. PATENT DOCUMENTS

| 3,888,866 | A | 6/1975 | Leute et al. |
| 4,197,237 | A | 4/1980 | Leute et al. |
| 4,207,307 | A | 6/1980 | Kaul et al. |
| 5,808,074 | A | 9/1998 | Gowda et al. |
| 6,174,723 | B1 | 1/2001 | Yugawa et al. |
| 6,271,381 | B1 | 8/2001 | Yugawa et al. |
| 6,541,004 | B1 | 4/2003 | Scherrmann et al. |

FOREIGN PATENT DOCUMENTS

WO    WO 97/21451    *  6/1997

OTHER PUBLICATIONS

William R. Thistle. Physchemidics RIA cocaine assay. 510 (K) summary, Nov. 6, 2001.*
Lu, Natalie, "Distinguishing Crack Use From Powder Cocaine: Indentification of Unique Pyrolysis Products from Crack Use In Urine", Apr. 26-30, 1999.
Jacob, Peyton III, et al., "A pyrolysis Product, Anhydroecgonine Methyl Ester (Methylecgonidine), is in the Urine of Cocaine Smokers", Journal of Analytical Toxicology, vol. 14, Nov./Dec. 1990.
Cone, Edward J., et al., "simultaneous Measurement of Cocaine, Cocaethylene, Their Metabolites, and "Crack" Pyrolysis Products by Gas Chromatography-Mass Spectrometry", 1994, pp. 1299-1305, vol. 40/7.

(Continued)

Primary Examiner—Long V. Le
Assistant Examiner—Shafiqul Haq
(74) Attorney, Agent, or Firm—Jon Tornquist

(57) ABSTRACT

A monoclonal antibody, and a cell line capable of producing the same, has been produced with the ability to detect the primary metabolites generated from the pyrolysis of smokeable, or "crack", cocaine. This monoclonal antibody, while being highly specific for anhydroecgonine methyl ester (AEME) and ecgonidine (ECD), does not cross-react at a significant level with the primary cocaine metabolites of powdered or injected cocaine. Also, crack cocaine conjugates capable of evoking an immune response in animals have been produced.

16 Claims, 2 Drawing Sheets

OTHER PUBLICATIONS

Levin, Barry, et al., "Stability of Ecgonine Methyl Ester in Postmortem Urine Specimens", Journal of Forensic Science, JFSCA, vol. 41, No. 1, Jan. 1996, pp. 126-128.

Riley, K. Jack, Natalie T. Lu, et al., "Monitoring the Crack Epidemic through Urine Testing: Establishment of Routine Detection Methods", Addiction Biology, 2001, pp. 83-95.

Pascal, Kintz, et al., "Testing Human Hair and Urine for Anhydroecgonine Methyl Ester, a Pyrolysis Product of Cocaine", Journal of Analytical Toxicology, vol. 19, Oct. 1995 pp. 479-482.

Cone, Edward, Validity of Commercial Urine Cocaine Metabolite Assays: III. Evaluation of an Enzyme-Linke Immunosorbent Assay (ELISA) for Detection of Cocaine and Cocaine Metabolite Journal of Forensic Sciences, vol. 34, No. 4, Jul. 1989, pp. 991-995.

Cone, Edward, et al., Validity Testing of Commercial Urine Cocaine Metabolite Assays: IV. Evaluation of the EMIT d.a.u. Cocaine Metabolite Assay in Quantitative Mode for Detection of Cocaine Metabolite, Journal of Forensic Sciences, vol. 35, No. 4, Jul. 1990, pp. 786-791.

Romberg, Robert W. and Past, M.R., "Reanalysis of Forensic Urine Specimens Containing Benzoylecgonine and THC-COOH", Journal of Forensic Sciences, vol. 39, No. 2, Mar. 1994 pp. 479-485.

Jeffcoat, Robert A., et. al., "Cocaine Disposition in Humans After Intravenous Injection, Nasal Insufflation (Snorting), or Smoking", Drug Metabolism and Disposition, vol. 17, No. 2, 1989 pp. 153-159.

Martinez, Francisca, et al., Cocaine Metabolite (Benzoylecgonine) in Hair and Urine of Drug Users, Journal of Analytical Toxicology, vol. 17, May/Jun. 1993, pp. 138-142.

* cited by examiner

Chemical Configuration of Several Immunogens

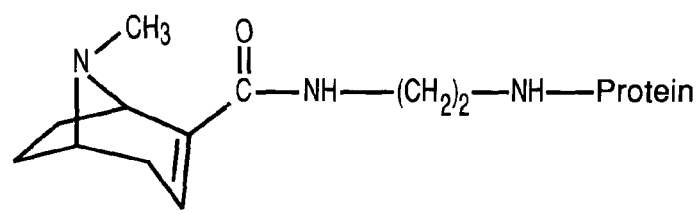

The structure of Ecgonidine (ECD) with EDA linker protein conjugates

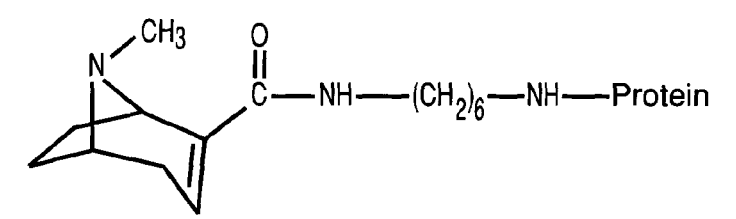

The structure of Ecgonidine (ECD) with HDA linker protein conjugates

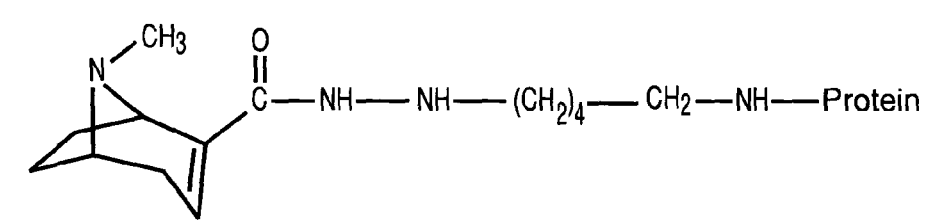

The structure of AEME with Glutaraldehyde linker protein conjugates

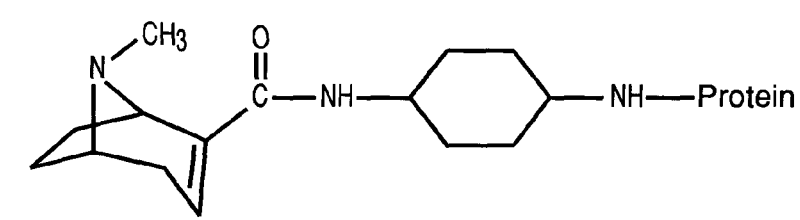

The structure of Ecgonidine (ECD) with CDA linker protein conjugates

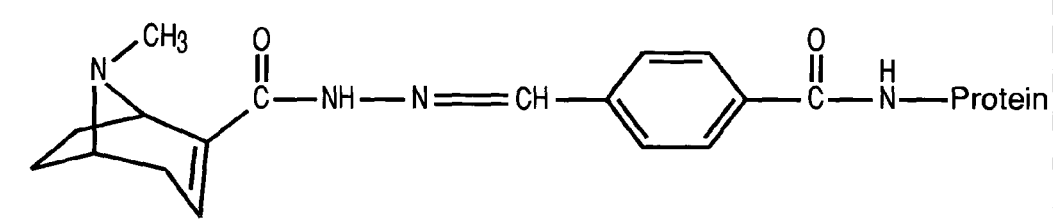

The structure of AEME with CBA linker protein conjugates

FIG.2

MONOCLONAL ANTIBODIES SPECIFIC FOR CRACK COCAINE METABOLITES, A CELL LINE PRODUCING THE SAME, AND CRACK COCAINE CONJUGATES

BACKGROUND OF THE INVENTION

1. Field of the Invention

This invention relates to a monoclonal antibody and a cell line capable of producing the same which may be used to detect various crack cocaine metabolites in a sample. This invention also relates to immunogens in the form of crack cocaine conjugates used to evoke an immune response in animals.

2. Background

When cocaine enters the human body it is quickly broken down into various metabolites. These metabolites are longer lived than the cocaine itself and thus may be assayed to determine if an individual has previously ingested cocaine. Various methods have been utilized to determine whether these metabolites are present in a sample, for example, immunoassays and gas chromatograph/mass spectrometer (GC/MS).

Gas chromatography/mass spectrometry is a highly sensitive and specific diagnostic tool for determining the presence and concentration of chemicals in a sample. However, it is expensive, time-consuming, and labor intensive; therefore, immunoassays, which are cheaper and quicker, are commonly used as an initial screening stage. Those samples which test positive using an immunoassay are frequently confirmed by gas chromatography to verify the presence of the metabolites.

Immunoassays detect their target chemical by utilizing antibodies which are raised to be specific for the particular chemical or closely related compounds. These antibodies have the ability to selectively bind to the chemical(s) in question while generally not binding to other chemicals in the sample. Thus, antibodies are quite useful in detecting the presence of chemicals in a sample even at nanogram per milliliter levels.

Antibodies specific for cocaine metabolites have previously been developed and produce highly sensitive diagnostic tests for detecting cocaine use. Currently available tests utilize monoclonal antibodies with a high affinity to a specific metabolite of cocaine, benzoylecogonine (BE); BE is used in these tests because it is the metabolite with the highest concentration several days after cocaine ingestion.

In the 1980's a smokable form of cocaine, "Crack" cocaine, became increasingly prevalent. Crack cocaine is a highly potent and addictive substance. Smoking, chemically referred to as pyrolysis, of crack cocaine produces distinctive metabolites such as anhydroecgonine methyl ester (AEME) and ecgonidine (ECD) which are not present in users of the powdered or injected forms of cocaine.

The addiction associated with crack cocaine and its particular central nervous system distribution leads to clinical complications that are different from powdered or injected cocaine use. In addition, criminal penalties for crack cocaine are potentially different than those of the powdered or injected forms. Despite the need for a test able to discriminate between the use of crack cocaine and cocaine's other forms, until now, no immunoassay or monoclonal antibody was able to selectively detect the use of crack cocaine versus the powdered or injected forms of the drug. Commercial immunoassays can detect only BE which is produced in both powdered and crack cocaine users. As there are specific clinical and legal implications for crack cocaine use, the need for monoclonal antibodies capable of distinguishing between the use of crack cocaine and the powdered or injected form, is evident.

BRIEF SUMMARY OF THE INVENTION

The invention relates to a monoclonal antibody with affinity for anhydroecgonine methyl ester, a metabolite specific to the use of crack cocaine.

The invention relates to a monoclonal antibody with affinity for anhydroecgonine methyl ester (AEME) and ecgonidine (ECD).

The invention aims to provide a cell line capable of producing monoclonal antibodies with affinity for anhydroecgonine methyl ester.

The invention further provides a cell line capable of producing monoclonal antibodies with affinity for ecgonidine and anhydroecgonine methyl ester.

The invention further aims to provide a method of producing a cell line capable of producing monoclonal antibodies with affinity for anhydroecgonine methyl ester.

The invention further aims to provide a method of producing a cell line capable of producing monoclonal antibodies with affinity for ecgonidine and anhydroecgonine methyl ester.

The invention further aims to provide immunogens capable of provoking an immune response in animals sufficient to create antibodies specific for crack cocaine metabolites; such as anhydroecgonine methyl ester and ecgonidine.

DEPOSIT OF BIOLOGICAL MATERIALS

The hybridoma cell line, described herein, was deposited on Mar. 28, 2003, under the conditions of the Budapest Treaty with American Type Culture Collection (ATCC) located at 10801 University Blvd., Manassas, Va. 20110 and was assigned the following number: PTA-5096.

BRIEF DESCRIPTION OF THE SEVERAL VIEWS OF THE DRAWINGS

FIG. 2 illustrates various chemical formulas of crack cocaine conjugates.

DETAILED DESCRIPTION OF THE INVENTION

Figure 1:
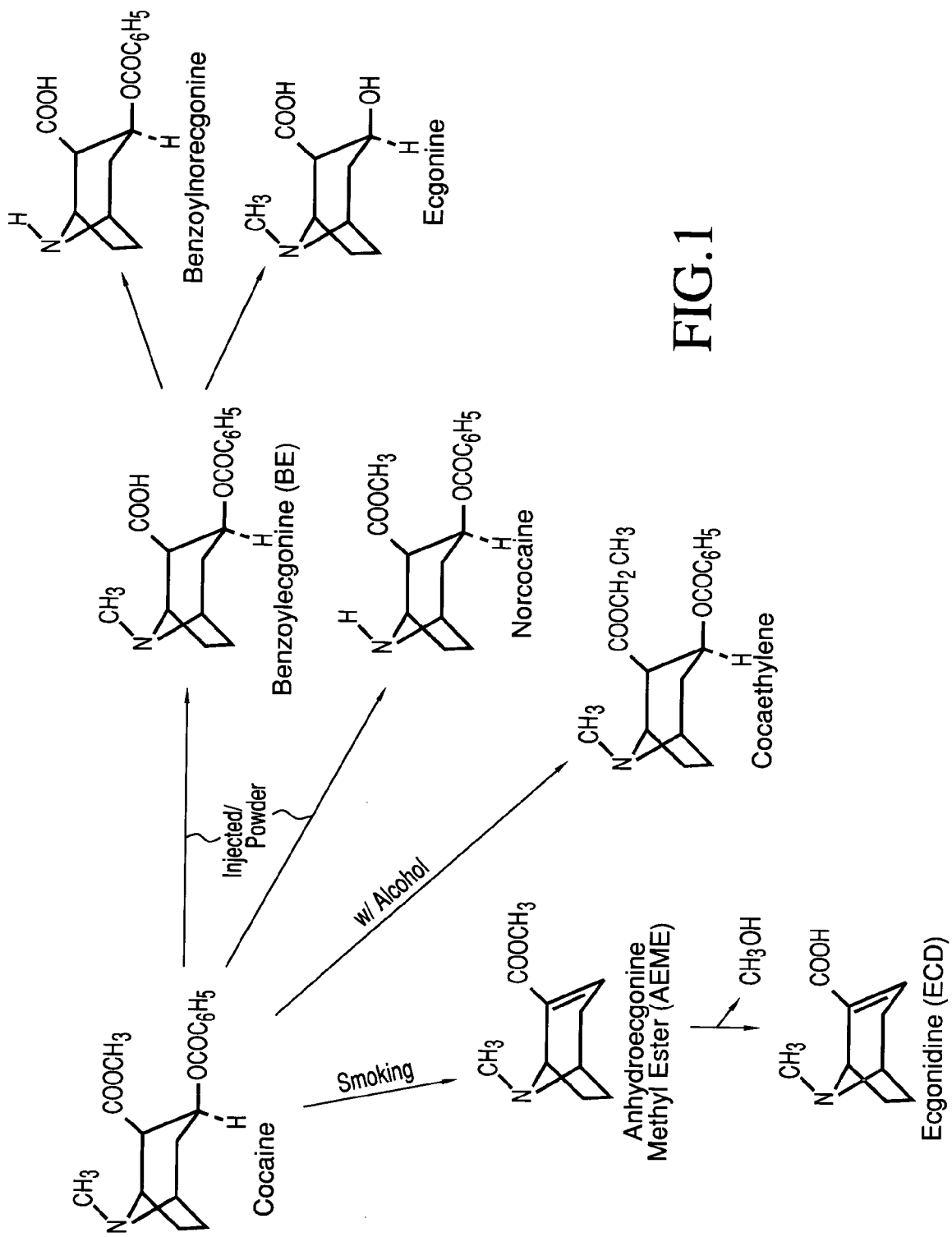
FIG. 1 illustrates the primary by-products of cocaine ingestion, including the primary by-products of cocaine ingestion and those produced through smoking and ingestion of cocaine concurrent with alcohol consumption.

In the invention, monoclonal antibodies with an affinity for AEME and ECD and a cell line capable of producing such antibodies are described. Also, immunogens capable of evoking a sufficient immune response to create antibodies specific for a crack cocaine metabolite are produced.

For the purposes of this patent, chemicals produced through either pyrolysis or metabolic pathways are considered metabolites and the term crack cocaine is intended to cover all forms of smoked or heated cocaine. In addition, crack cocaine metabolites are defined as those chemicals which are present in crack cocaine users but are not present in significant amounts in powdered or injected cocaine users.

Preparation of Cell Line and Antibodies

The process of preparing a monoclonal antibody producing cell line comprises the steps of creating an immunogen in the form of a metabolite or a metabolite chemically combined with an immunogenic carrier and/or linker molecule, immunizing a host animal with this immunogen, testing for antibody production, removing cells from those animals producing adequate amounts of the desired antibodies, fusing these cells with a continuously expanding cell line to produce a rapidly expanding hybrid cell line, selectively screening the resulting hybrid cells for antibody production, and separating, expanding, and storing those cells which show adequate specific antibody production.

A. Immunization

1. Creation of Immunogen

Many small foreign molecules will not induce an immune reaction, or will only produce one of limited strength. Therefore, in order to ensure immuno-reactivity, a macromolecule known to induce immune reactions may be chemically attached to the metabolite. The macromolecule, or carrier, used can be quite varied as animals can make antibodies against virtually any chemical group. The best macromolecule carrier for a particular metabolite must be determined through experimentation as it depends on the test animal and the antigen.

Macromolecules with antigenic properties include proteins, polypeptides, dyes, enzymes, antibodies, carbohydrates, complex lipids, nucleic acids and polysaccharides. It has been found that proteins and preferably proteins from the group of bovine serum globulin (BSG), keyhole limpet hemocyanin (KLH), ovalbumin (OVA), and bovine serum albumin (BSA), are effective carriers of crack cocaine metabolites.

In addition to the attachment of a carrier molecule, often the use of a spacer sequence is necessary. A spacer, or linker, molecule is often needed because, depending on the chemical configuration of the metabolite and carrier, the carrier may mask the metabolite of interest. Therefore, a linker molecule is used to separate the metabolite from the carrier and allow the immune system to specifically recognize the metabolite apart from the carrier. Several types of linkers may be used such as: HDA(diaminohexane), CDA (diaminocyclohexane), EDA (ethylenediamine), Glut (glutaraldehyde), and CBA (carboxybenzaldehyde). Whether a linker molecule is needed, and which one to use depends upon the metabolite, linker, carrier, and animal used.

The chemical synthesis of both the antigen-carrier and antigen-linker-carrier complexes is known in the art and is not limited in this invention to any particular method.

2. Immunization of the Animal

After creation of the crack cocaine metabolite-carrier conjugate, the animal of choice is injected with this immunogen several times at intervals between two and three weeks. In the preferred embodiment, four immunization injections have been found to be effective in stimulating an immune response. If selected as a candidate for fusion, the animal is given one additional injection of the immunogen within one week of the fusion procedure as a booster in order to ensure adequate immune response.

A variety of animal types known in the art may be used to practice this invention, but mice are the animal of choice. Different kinds of mice can be used, such as, but not limited to, A/J, BALB/c, CAF(1), Swiss, Nude or Fox Chase SCID mice. The preferred results were obtained through the use of Swiss type mice. It should be noted that the immune response of a particular type of mouse type depends on the metabolite-spacer-carrier immunogen used.

B. Creation of Hybrid Cells.

After immunization sera from the host animal is removed and examined by enzyme-linked immunoabsorbent assay (ELISA) for antibodies to the metabolite of choice.

If the host animal is found to have acceptable sera antibody activity, cells, usually in the form of splenocytes, are removed from the animal. These cells are then fused with a myeloma cell line. The preferred myeloma cell line is P3×63Ag8.653. However, other cell lines known in the art may be used effectively. These cells may be selected using techniques known in the art and may consist of any effective continuously replicating tumor cells.

Fusion of the two cells may be performed using techniques known in the art. One common method is the use of polyethylene glycol to fuse the myeloma cell line to the splenocyte to create a hybridoma.

The resulting hybridomas are then screened by ELISA. Hybridomas producing monoclonal antibodies of sufficient specificity may then be used to produce larger quantities of monoclonal antibodies or may be frozen and cryopreserved for future use.

C Detecting AEME or ECD in a Sample Using the Monoclonal Antibodies.

Not all monoclonal antibodies are sufficiently specific for the presence AEME or ECD to be effective. Often the monoclonal antibodies cross-react with both cocaine and BE (the primary metabolite of standard cocaine ingestion) producing a false positive indication of crack cocaine ingestion. While some cross-reactivity is normal and inevitable, beyond a certain threshold too great a cross-reactivity will make the antibody useless in standard diagnostic tests. This is due to the fact that the antibody will bind to, and thus produce positive response to, the most common metabolites of both crack and powdered or injected cocaine ingestion.

In the preferred embodiment, the effective monoclonal antibody for crack cocaine detection, as used in standard testing protocols, should preferably have a specificity, or the ability to detect at concentrations of $AEME \leq 50$ ng/ml and $ECD \leq 500$ ng/ml, and preferably, $ECD \leq 100$ ng/ml, while not cross-reacting with concentrations of cocaine below 2 ug/ml or BE below 10 ug/ml.

Cell lines produced using AEME or AEME conjugates as the immunogen, in general, produce poor monoclonal antibodies for ECD. By contrast, and unexpectedly, the ECD immunized animals often produce monoclonal antibodies with high affinity to both AEME and ECD.

In addition, it has been found that ECD exist in a ratio of 10 to 20 times (10:1 to 20:1) the amount of AEME at any given time in urine samples of crack cocaine users. The antibodies of the invention, surprisingly, display the same ratio of sensitivity, i.e., AEME is detected at 10 to 20 times lower concentrations than ECD.

D. Antibody Production

When monoclonal antibodies are desired a limited dilution cloning is performed to insure monoclonality of the cell line. The selected clones are then multiplied, or expanded, in either mice or tissue culture.

1. Mice

After fusion the clones are injected into the cavity of a target mouse at a level of one million cells per mouse. After two to three weeks ascites are recovered from the mouse and processed and purified by placing the ascites on a Protein-A Sepharose column.

Generally, the production of monoclonal antibodies in mice, while an expeditious way to produce and test clones, is limited by the small quantities recovered and the expense of caring for the animals. When significant quantities are desired, cell culture in vitro is preferred.

2. Tissue Culture.

Selected hybridoma cells are removed from cryogenic stasis and thawed. These cells are then expanded in T-162 flasks followed by transfer to roller bottles with growing media for the particular type of cells selected for cloning, a method known in the art for producing cell supernatant. Two weeks after transfer into roll bottles the majority of cells have died and the supernatant is harvested for purification.

It is then necessary to separate the monoclonal antibodies from the rest of the contents of the flask. This is done through purification; while Protein-A Sepharose purification is preferred, any standard antibody purification method known in the art may be used.

The following examples are intended to illustrate the invention and are not intended to limit the scope of the invention described in the claims.

EXAMPLE 1

Preparation of a Cell Line Capable of Producing Antibodies Specific for ECD and AEME.

(1) Preparation of the Antigen.

To prepare the antigen commercially available ECD and AEME were selected. Several combinations of antigen, antigen-carrier, and antigen-linker-carrier were created using standard methods known in the art. These combination were: ECD, AEME, ECD-BSA, ECD-KLH, ECD-OVA, AEME-BSA, AEME-KLH, ECD-EDA-BSA, ECD-HDA-BSA, ECD-HDA-KLH, ECD-HDA-OVA, ECD-CDA-KLH, AEME-Glut-BSA, AEME-CBA-KLH, ECD-EDA-KLH, and AEME-Phenyl-BSA.

All conjugates were purified by dialysis methods known in the art and were tested using Ultraviolet (UV) spectrometry at 254 and 280 nm. Final concentrations of conjugates were 0.5 mg/ml.

By using Swiss and BALB/c mice immunized with ECD-BSA, ECD-KLH, AEME-Phenyl-BSA, AEME-BSA, or AEME-KLH immunogens, monoclonal antibodies with high specificity for AEME but not ECD were produced. The best monoclonal antibodies from this immunization set were produced using ECD-KLH in Swiss mice and had a specificity of 4.2 ng/ml (50% reactivity) of AEME and 100 ng/ml of ECD. A second set of immunizations utilizing various linker molecules produced a monoclonal antibody capable of detecting ECD at<100 ng/ml.

After immunization of various types of mice with the varied antigen complexes, it was determined that the preferred complex for production of monoclonal antibodies with specificity for ECD and AEME was ECD-EDA-KLH in Swiss type mice.

(2) Immunization

The most effective immunization of the target animals was completed using the antigen-linker-carrier complex (immunogen) of ECD-EDA-KLH. A total of five Swiss mice were immunized with this particular combination.

The mice were immunized by injecting between 0.25–0.50 ug of the immunogen (consisting of 2.5 mg/ml ECD-EDA-KLH diluted in PBS for a final concentration of 0.5 mg/ml) emulsified with complete Freund's adjuvant into the intra-peritoneal cavity of the mice. This was followed by three more booster injections conducted at two week intervals, composed of the immunogen (consisting of 2.5 mg/ml ECD-EDA-KLH diluted in PBS for a final concentration of 0.5 mg/ml) emulsified with incomplete Freund's adjuvant.

One week after each booster injection, the mice were bled and their sera collected and titrated by ELISA against both ECD and AEME. The mice having the highest titer and monoclonal antibody specificity were selected for fusion.

(3) Fusion

Those animals selected for the fusion procedure were given a booster injection four days prior to the procedure using the same immunogen used to produce the original immune reaction (consisting of 2.5 mg/ml ECD-EDA-KLH diluted in PBS for a final concentration of 0.25 mg/ml) but without the adjuvant.

On the day of the fusion procedure, for each mouse selected, the mouse was sacrificed and the spleen removed. The spleen was then minced using forceps and strained through a sieve. The cells were then washed twice using IMDM (Iscove's Medium) and counted using a hemocytometer.

The myeloma cell line P3×63Ag8.653 was then removed from a separate culture and washed with IMDM. The myeloma and spleen cells were mixed in a 1:5 ratio and centrifuged. The supernatant was discarded and the cell pellets resuspended in the tube while adding one milliliter of a 50% solution of Polyethylene Glycol (PEG (MW 1450)) drop by drop over a period of 30 seconds. Five milliliters of IMDM were then added over a period of 90 seconds immediately followed by another 5 milliliters.

The resulting cell suspension was left undisturbed for five minutes and then spun in a centrifuge to create cell pellets. These pellets were then resuspended in HAT medium, which consisted of IMDM containing 10% FBS (Fetal Bovine Serum), 2 mM L-glutamine, 0.6% 2-mercaptoethanol (0.04% solution), hypoxanthine, aminopterin, thymidine, and 10% Origen growth factor. The cells were then resuspended to 500,000 cells per millilter and then plated into 96 well plates at a rate 10,000 cells per well.

These plates were then incubated at 37 C in a 7% carbon dioxide atmosphere with 100% humidity. Seven days after fusion the media was removed and replaced with IMDM containing 10% FBS, 2 mM L-glutamine, 0.6% 2-mercaptoethanol stock (0.04%), hypoxanthine and thymidine.

Ten to fourteen days after fusion, the supernatant was taken from the wells with growing hybridoma colonies. This supernatant was then tested for specific antibody activity using the same assay used to screen the sera. Positive hybridoma colonies were then transferred from the 96 plate well to a 24 well plate. After three to five days the supernatant from the 24 well plate was tested to confirm the presence of specific antibody activity for ECD and AEME.

A total of 100 positive hybridomas were obtained from this process. After cross reactivity testing, 9 hybridomas were selected as possessing the necessary specificity; that is the ability to bind to a crack cocaine metabolites such as AEME and ECD while lacking significant cross-reactivity to cocaine or BE. Further reactivity testing determined the three best monoclonal cell lines were: 181A 356.1, 181A 958.1, and 181A 1026.1 (internal laboratory assignments). Each of these three cell lines produced monoclonal antibodies of isotype IgG2a, k.

The cell line 181A 356.1, which was deposited with ATCC (PTA-5096), was selected as the preferred clone because it possessed a sensitivity of 1.2 ng/ml against AEME and 27.7 ng/ml against ECD while showing no significant cross reactivity to concentrations of cocaine below 7.8 ug/ml and BE below 10 ug/ml.

(5) Storage.

Having selected the 181A 356.1 cell line as the preferred monoclonal antibody producing hybridoma, the cell line was expanded and then frozen for storage.

The cells to be frozen were first centrifuged to produce cell pellets and were then resuspended in a medium of 10% DMSO and 90% Fetal bovine serum. The cells were quickly placed into vials and frozen in a liquid nitrogen freezer.

It is preferred that the cell line is stored at a density between $5 \times 10^6$–$1 \times 10^7$ cells/mL, with one mL per vial.

EXAMPLE 2

Production of Monoclonal Antibodies from the Chosen Cell Lines.

Selected hybridoma cells were removed from cryogenic stasis and thawed. In order to maximize success, only healthy cells that were in the exponential phase of growth and 85% viable at the start of the procedure were used. Using an inverted microscope, the cell culture was visually examined for the presence of bacterial contamination. Then the cell count was taken and the percent viability of the cells was determined. The rate at which a cell line is expanded depends upon its doubling time. Typical bottle seeding densities are between $5 \times 10^4$ and $2 \times 10^5$ cells/ml, which allows for 2–3 days of growth before the cells need fresh media.

The standard 850 cm² (1 liter) roller bottles holding 400–600 ml culture were then seeded with the cells. These cells were expanded in T-162 flasks followed by transfer to roller bottles for production of cell supernatant using Basal Medium. The roller bottles were gassed with a 10% $CO_2$/90% atmosphere mixture. Then a sterile cotton plugged pipet was connected to a sterile rubber tube hooked to a 10% $CO_2$/90% atmosphere gas cylinder. Care was taken not to allow the pipet to touch the roller bottle or media inside the roller bottle. Gas was then admitted into the roller bottle for 20 seconds. The gas pressure was just sufficient to cause a ripple effect on the liquid surface. After the roller bottle was gassed, the top on bottle was sealed as quickly as possible using the screw cap.

Roller bottles were then placed in a roller bottle cabinet. The cabinet was set at 37° C. and 1.9–2.0 RPM. Roller bottles were then examined daily using an inverted microscope. When cells appeared to be approaching maximum cell density, a 0.5 mL sample of culture was aseptically collected for a cell count and percent viability reading. The cell count and viability dictated whether the cells were ready for harvest or re-feeding (splitting). All bottles that were opened were then re-gassed. Approximately two weeks after transfer into roll bottles the majority of cells died and the supernatant was harvested for purification on a Sepharose A column.

EXAMPLE 3

Sample Chemical Conjugation of ECD to BSA without a Linker.

The following procedure may be used to synthesize ECD conjugated to a protein.

First, 10.0 mg of ECD (0.0598 mM) plus 34.4 mg of 1-[3-(Dimethylamino) propyl]-3-ethylcarbodiamide hydrochloride (EDC) (0.1794 mM) plus 20.6 mg of N-Hydrosuccinimide (NHS) (0.1794 mM) are mixed with 1 ml of N,N-Dimethylformamide (DMF). The mixture is stirred at room temperature overnight.

Then, 10.0 mg of BSA (protein) in 2.0 ml of dicarbonate buffer, pH 9.6, is added to 75.3 uL of the reacted NHS-EDC ester. The mixture should be stirred at room temperature over night.

The reacted BSA-ECD solution should then be dialyzed against 1 L of PBS buffer, pH 7.2, with two buffer changes. The dialyzed BSA-ECD conjugate solution may then be harvested

EXAMPLE 4

Sample Conjugation of ECD with EDA Linker.

The following procedure may be used to synthesize ECD conjugated to a linker and a protein.

First, 10.0 mg of ECD (0.0598 mM) plus 34.4 mg of 1-[3-(Dimethylamino)propyl]-3-ethylcarbodiamide hydrochloride (EDC) (0.1794 mM) plus 20.6 mg of N-Hydrosuccinimide (NHS) (0.1794 mM) are mixed with 1 ml of N,N-Dimethylformamide (DMF). The mixture is stirred at room temperature overnight.

Then, 10.0 mg of BSA in 1.0 ml of MES buffer (0.01 M), pH 4.7, is added with 13.3 mg of ethylenediamine dihydrochloride (EDA) and 10.0 mg of EDC. The mixture is stirred at room temperature over night.

The reacted BSA-EDA solution is dialyzed against 1 L of PBS, pH 7.2, with two buffer changes. The BSA-EDA conjugate is harvested.

Then, 5.0 mg of BSA-EDA solution is added to 37.6 ul of the reacted ECD-NHS solution and the mixture is stirred at room temperature over night. The reacted BSA-ECD solution is then dialyzed against 1 L of PBS (pH 7.2) with two buffer changes. The BSA-EDA-ECD conjugate is then harvested.

The invention claimed is:

1. A monoclonal antibody having a specificity for anhydroecgonine methyl ester.

2. A monoclonal antibody having a specificity for both anhydroecgonine methyl ester and ecgonidine.

3. A hybridoma cell line which produces a monoclonal antibody with a specificity for anhydroecgonine methyl ester.

4. A hybridoma cell line which produces a monoclonal antibody having a specificity for anhydroecgonine methyl ester and ecgonidine.

5. A hybridoma cell line PTA-5096 which produces a monoclonal antibody having a specificity for anhydroecgonine methyl ester and ecgonidine.

6. A method for creating a hybridoma cell line capable of producing a monoclonal antibody with specificity towards a crack cocaine metabolites anhydroecgonine methyl ester and ecgonidine comprising the steps of:
   a. producing an immunogen comprising a crack cocaine metabolites anhydroecgonine methyl ester and ecgonidine conjugated to an antigenic carrier; and
   b. immunizing an animal with said immunogen; and
   c. fusing a cell from said immunized animal with a continuously dividing cell to create a fused cell capable of producing a monoclonal antibody with a specificity for a crack cocaine metabolite; and
   d. cloning said fused cell.

7. The process of claim 6, wherein said animal is a mouse selected from the group consisting of A/J, BALB/c, CAF(1), Swiss, and Nude and Fox Chase SCID.

8. The process of claim 7 wherein said antigenic carrier is a protein selected from the group consisting of: bovine serum globulin (BSG), keyhole limpet hemocyanin (KLH), ovalbumin (OVA), and bovine serum albumin (BSA).

9. The process of claim 6 wherein a linker molecule is inserted between said metabolite and said antigenic carrier.

10. The process of claim 9 wherein said linker molecule is selected from the group consisting of: 1,6, Diaminohexane (HDA); 1,4 Diaminocyclohexane (CDA); Ethylenediamine (EDA); Carboxybenzaldehyde (CBA); and Glutaraldehyde.

11. An immunogen comprising a crack cocaine metabolites anhydroecgonine methyl ester and ecgonidine conjugated to an antigenic carrier.

12. The immunogen of claim 11, wherein said antigenic carrier is a protein.

13. The immunogen of claim 12, wherein said protein is selected from the group consisting of bovine serum globulin (BSG), keyhole limpet hemocyanin (KLH), ovalbumin (OVA), and bovine serum albumin (BSA).

14. An immunogen comprising a crack cocaine metabolites anhydroecgonine methyl ester and ecgonidine and which is linked to an antigenic carrier.

15. The immunogen of claim 14, wherein said antigenic carrier is a protein selected from the group consisting of bovine serum globulin (BSG), keyhole limpet hemocyanin (KLH), ovalbumin (OVA), and bovine serum albumin (BSA).

16. The immunogen of claim 15, wherein said linker molecule is selected from the group consisting of 1,6, Diaminohexane (HDA), 1,4 Diaminocyclohexane (CDA), Ethylenediamine (EDA), Carboxybenzaldehyde (CBA), and Glutaraldehyde.

* * * * *